Figure 1:
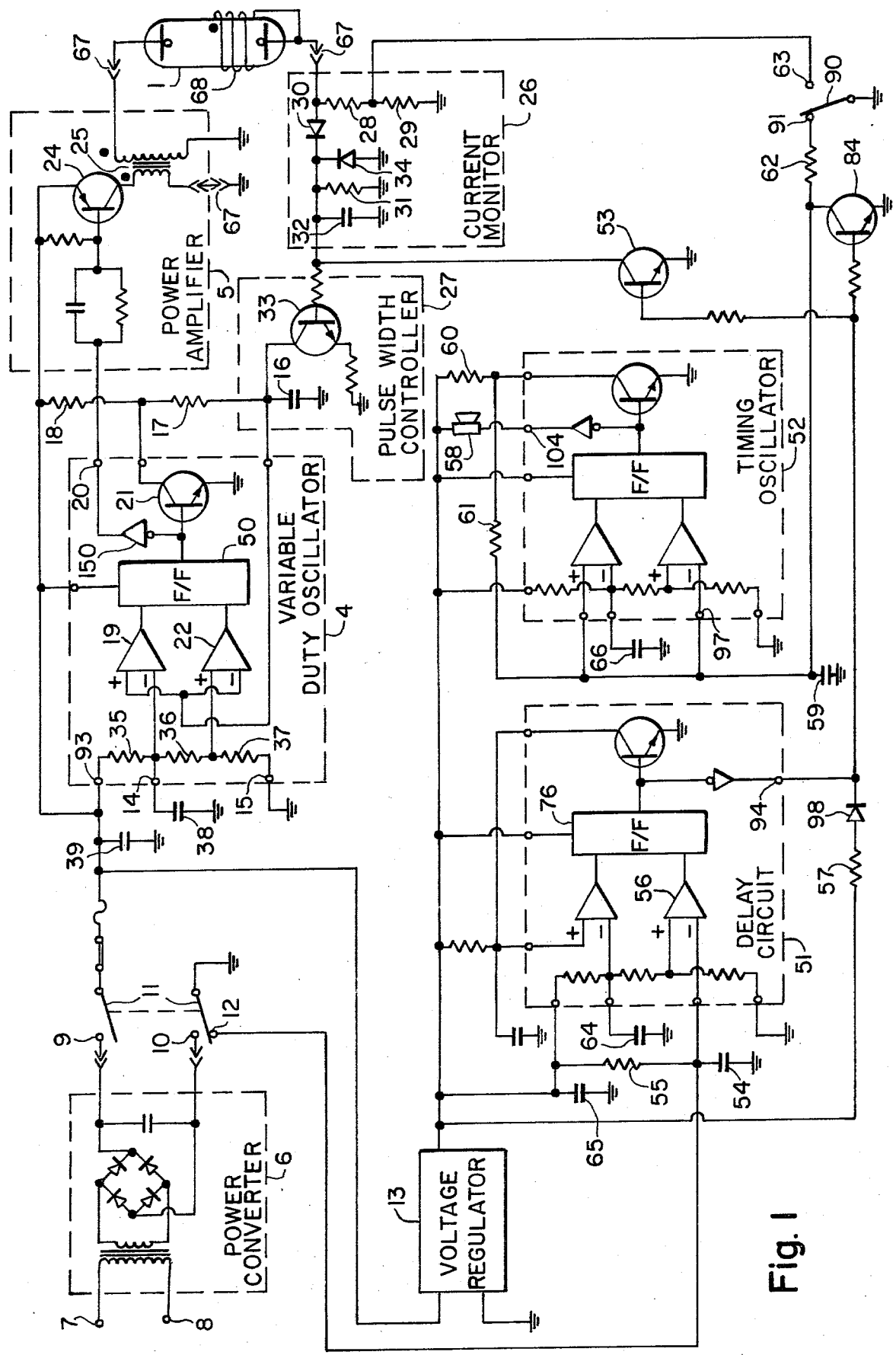

United States Patent [19]

Friedman et al.

[11] 4,221,994
[45] Sep. 9, 1980

[54] PHOTO CURING LIGHT SOURCE

[75] Inventors: Joshua Friedman, Ridgefield; Brian Dell, Newtown, both of Conn.

[73] Assignee: Demetron Research Corporation, Danbury, Conn.

[21] Appl. No.: 959,313

[22] Filed: Nov. 9, 1978

[51] Int. Cl.$^2$ .............................................. H05B 41/39
[52] U.S. Cl. .................................... 315/224; 250/493; 250/504 H; 315/307; 315/DIG. 7
[58] Field of Search ................. 315/224, 307, DIG. 5, 315/DIG. 7; 250/493, 504

[56] References Cited
U.S. PATENT DOCUMENTS

| | | | |
|---|---|---|---|
| 3,648,106 | 3/1972 | Engel et al. | 315/307 X |
| 3,890,537 | 6/1975 | Park et al. | 315/307 X |
| 3,970,856 | 7/1976 | Mahaffey et al. | 250/493 |
| 4,112,335 | 9/1978 | Gonser | 315/241 R |

FOREIGN PATENT DOCUMENTS 2642972 3/1978 Fed. Rep. of Germany ........... 315/307

*Primary Examiner*—Eugene R. LaRoche
*Attorney, Agent, or Firm*—Bernard Ouziel

[57] ABSTRACT

A compact, lightweight source of radiation at wavelengths ranging from long wave ultraviolet through the visible powered from a low power DC source wherein a high frequency oscillator provides regulated driving current for the excitation of a fluorescent tube which emits energy at wavelengths outside the erythemal zone and wherein a first level of energizing current is provided for a warmup of the tube, a second level of energizing current is provided for standby excitation and a third level of energizing current is available for more intense operating excitation during which time there is also provided an audible timing signal.

8 Claims, 2 Drawing Figures

PHOTO CURING LIGHT SOURCE

The present invention relates to an instrument for generating electromagnetic radiation and more particularly to a power efficient, compact, controlled, photocuring light source for use in hardening photosensitive reactants such as dental restorative material.

For many years dentists have used silver amalgams for filling dental cavities and for other dental restoration. In using such materials dentists were required first to spend a portion of their time mixing the silver and mercury which, when ready, had to be placed quickly in the oral cavity during the period of time the material remained pliable. Thereafter, the dentist was required to suffer still another delay until the material was fully set before it could be shaped to the desired contours. It was not acceptable for use on anterior teeth because of its dark color.

The requirement of speedy enplacement of a restorative material, which eliminates the periods of unproductive time consumed in mixing the material and waiting for it to set, as well as the time involved in finishing after the material has set, has led to the development of substitute dental restorative materials which avoid these disadvantages. A class of such improved dental restorative material referred to as composites is made from unpolymerized organic photosensitive reactant materials, now commercially available to dentists. These photosensitive reactants may be taken from a container and placed directly within the oral cavity where they remain pliable to permit the dentist to immediately construct the desired contours without the need for undue haste. Only after the dentist has achieved the contours desired, is the dental restorative material hardened or cured. This may be done within 20 seconds by exposing it to a source of suitable photocuring radiation which may lie within the long wave ultraviolet and the visible range of wavelengths. These materials match the tooth color extremely well and may be used on anterior as well as posterior teeth.

A number of instruments have been developed to deliver photocuring light needed to harden such dental restorative material. Existing instruments, however, suffer from certain disadvantages which have limited their utility. For example, a number of such instruments use mercury vapor or incandescent tungsten lamps to produce radiation. The radiation is delivered by a light conducting source such as a quartz rod, a fiber optic, or a fluid filled bundle, to an illuminating probe that fits within the oral cavity. These units are large and cumbersome, and require filters and shields to minimize the dangers of exposure to short wave ultraviolet energy generated by mercury vapor lamps known to induce erythema in the tissues. They also require large quantities of operating power which produces unwanted heat that prohibits continuous prolonged use. In consequence, these instruments require expensive and bulky cooling means to permit even limited operation.

Another instrument known in the prior art uses a fluorescent type tube ignited by a 60 cycle line current and operated with a current limiting ballast. While this instrument eliminates some of the disadvantages inherent in those described above,—e.g. the need for extensive and cumbersome filters and shields to guard against leakage of short wave erythemal ultraviolet light and the inefficient transmission of light from the source to the probe—certain other disadvantages persist. For example, the power source for the fluorescent lamp requires a large expensive and inefficient ballast transformer. Since it operates at 60 cycles, it does not produce sufficient output energy and therefore requires greatly extended exposure time for curing this class of material.

Accordingly, the objectives of our invention are to provide a compact, efficient, controlled, versatile radiation source that may be conveniently used within the oral cavity for curing photosensitive dental restorative materials.

In meeting these objectives, we have provided a lamp powered by a low power DC source. The DC power source plugs into and converts conventional AC line power and is physically separated from the patient. Photocuring light is obtained from a miniature fluorescent lamp within a probe designed to fit within the oral cavity and driven by a variable duty high frequency oscillator.

Other features of our invention include means for monitoring and regulating the current through the fluorescent tube by adjusting the duty cycle of the oscillator; a mode switch to limit the current to the fluorescent tube while the instrument is on standby operation and to increase the current when the probe is removed from its holder for use in curing the dental restorative material; an indicator which advises the user when the unit is ready for use after a short warmup period; and an audible timing signal that advises the dentist of the elapsed exposure time.

Figure 2:
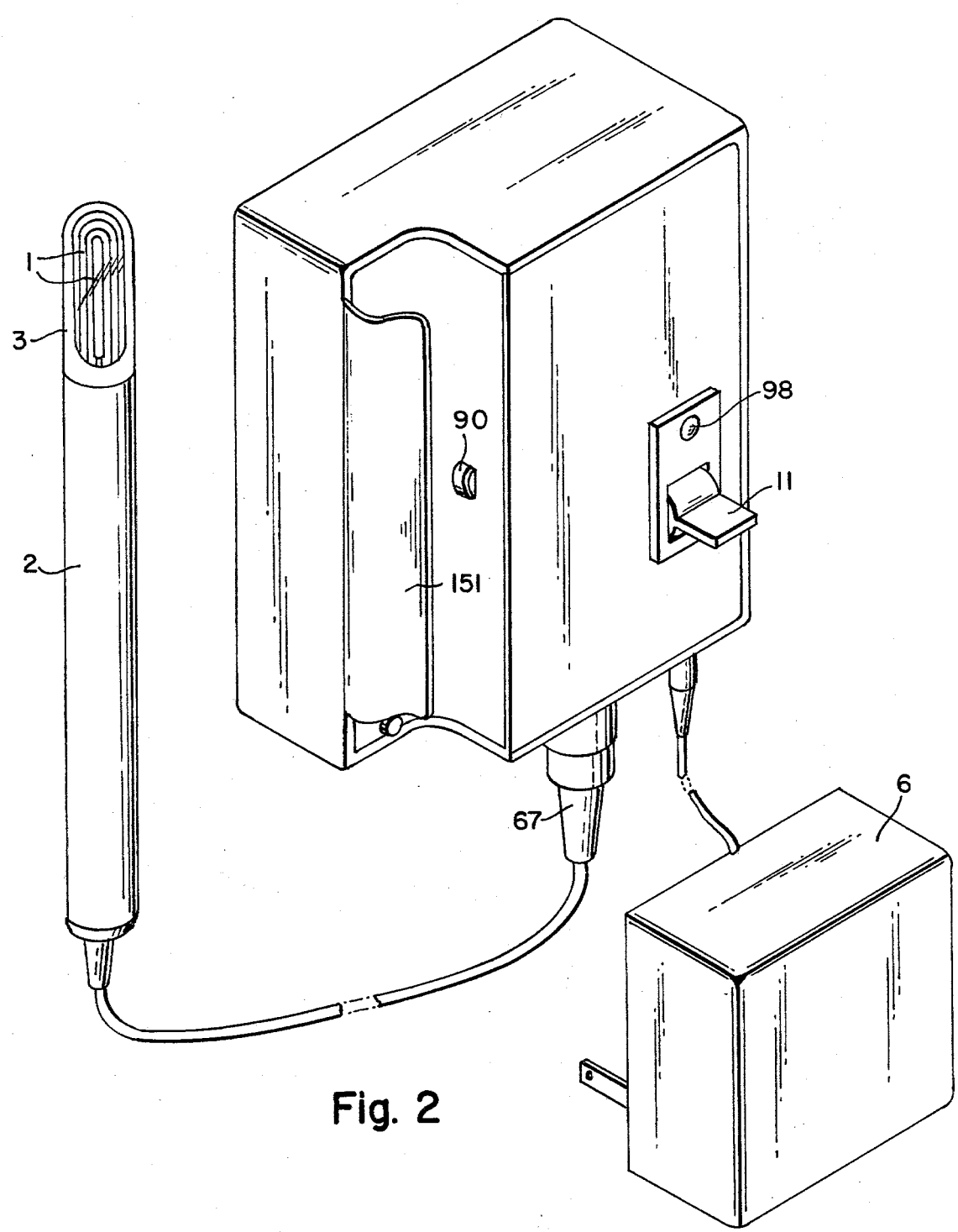

Our invention will be better understood if reference is had to the following detailed description and accompanying drawing in which:

FIG. 1—is a schematic circuit showing the means for energizing and controlling the fluorescent lamp used to generate the photocuring light;

FIG. 2—is a perspective view of the apparatus.

Referring now to the drawing, glass tube 1 is a fluorescent lamp internally coated with a phosphor layer which when excited emits photocuring radiation. The wavelength of this radiation is chosen to match the photosensitivity of the composite which may lie from the long wave ultraviolet into the visible, depending on the formulation of the composite. For example, one lamp emitting radiation peaked at 370 nm is used to cure ultraviolet sensitive composite, however other composites exist which are cured in the visible at 470 nm. By choice of phosphor coating many such composites may be cured. This allows the output of the lamp to be easily tailored to the specific curing wavelength of the material. In no case does any lamp emit radiation at wavelengths less than 310 nm and a negligible amount between 310 nm and 340 nm. This glass tube rests within a probe 2 having an acrylic transparent shield 3 which effectively filters out any minimal residual erythemal ultraviolet wavelengths produced, so that the output energy poses no hazard to the user. Fluorescent tube 1 is driven from a high frequency variable duty oscillator 4 and power amplifier 5 and may be in the shape of an oval as shown.

A power converter 6, which may be of the commercially available variety that plugs into wall outlets, converts 60 cycle line power at terminals 7 and 8 to a voltage on the order of 15 volts rectified DC at terminals 9 and 10. Power is delivered to the instrument by actuating a power-on switch 11, shown in its open position on FIG. 1.

Oscillator 4 may be any one of a number of timing circuits that are commercially available as integrated chips and which permit external control of the on-off time or duty cycle. One such oscillator is the Fairchild 555 timing circuit containing two voltage comparators 19 and 22 which drive an astable multivibrator flip-flop 50 as shown in FIG. 1.

The power circuit operates as follows:

At power-on, with the actuation of switch 11, approximately 15 volts DC appears at input terminal 93 of oscillator 4. With this, capacitor 16 in the pulse width controller 27 begins to charge through resistors 17 and 18. Resistors 35, 36 and 37 are equal in impedance so that when capacitor 16 exceeds ⅔ of the DC line voltage, comparator 19 actuates flip-flop 50 to switch terminal 20 (after the output of flip-flop 50 passes through inverting amplifier 150) from DC line voltage to ground. When this occurs, transistor 21 is turned on and capacitor 16 begins to discharge through resistor 17. When the voltage across capacitor 16 diminishes to slightly less than ⅓ of the DC line voltage, comparator 22 switches flip-flop 50 to return terminal 20 to the DC line voltage. With this, discharge transister 21 is switched off. Once again capacitor 16 begins to charge through resistors 17 and 18 and the cycle is repeated. It has been found desirable to select circuit values so that the flip-flop operates at 30–40 kilohertz, but other frequencies will perform adequately as will be understood by those versed in the art.

The output of oscillator 4 is fed to power amplifier 5 which contains an inverting transistor 24 and step-up transformer 25. The output from the power amplifier is fed directly to the fluorescent tube 1 at voltages approximating 1–2 kv or such other values as will be sufficient to cause ignition. Because the frequency of operation is much above that available at the AC line, transformer 25 can be greatly reduced in size and weight and still function as required.

As current continues to flow in tube 1, it increases in temperature, tending to increase further the flow of current which, if not controlled, will result in the destruction of tube 1. The current through fluorescent tube 1 is detected by current monitor 26, the output of which is fed through pulse width controller 27 which operates in the following manner. The current through fluorescent tube 1 is divided so that approximately one-half the DC component passes to ground through resistors 28 and 29 and the other half, after passing through diode 30, travels to ground through resistor 31. The values of resistors 28, 29 and 31 are selected to yield a control voltage across capacitor 32 on the order of 0.6 volts when the desired average current flows within lamp 1. This voltage is sufficient to cause transistor 33 to begin to turn on. With an increase in current through lamp 1, there is produced a corresponding increase in the voltage at the output of current monitor 26 and thus at base of transistor 33. This increase in voltage drives transistor 33 further into conduction to thereby bleed away from capacitor 16 some portion of both its charging and discharging currents. The consequent effect is to both lengthen the time between pulses at output terminal 20 and also to diminish the width of such pulses. The result is a decrease in the average power delivered to lamp 1, producing a reduction in the output voltage of current monitor 26 and a corresponding decrease in base voltage of transistor 33 until equilibrium is restored.

As is understood by those versed in the art, diode 34 is included within current monitor 26 to protect the base-emitter junction of transistor 33 from burnout during the negative portion of the oscillator duty cycle and capacitors 38 and 39 function as a bypass for extraneous AC signals appearing in the DC supply line.

As part of our invention we provide a voltage regulator 13 (which may be any commercially suitable monolithic chip) to supply a small amount of DC power at approximately 5 volts to the balance of the circuit which includes a delay circuit 51 and a timing oscillator 52 which drives an audible beeper 58. Delay circuit 51 and timing circuit 52 may be any suitable commercially available integrated chip (e.g. Fairchild 556) arranged to operate as a one-shot monostable and as an astable oscillator, respectively. Their internal components are similar to those appearing in variable duty oscillator 4.

In accordance with the features of our invention we provide three levels of power to operate the instrument. The first is available when the unit is first switched on and lamp 1 is cool and incapable of full output. When this condition exists, it is desirable to maximize the current through tube 1 to reduce warm-up time needed for it to reach working temperature. This is accomplished as follows: Capacitor 54, which had previously been discharged through contact 12 of switch 11 during power-off, now begins to charge from the voltage regulator output through resistor 55. The output voltage at terminal 94 of delay circuit 51 remains at a high level (approximately equal to the output of the voltage regulator) until the voltage across capacitor 54 exceeds ⅔ of the regulator output voltage. When this occurs after approximately two minutes, comparator 56 switches flip-flop 76 and the output voltage at terminal 94 drops to ground. Current now begins to flow from the voltage regulator through resistor 57 to energize light emitting diode 98 and to indicate visually that fluorescent tube 1 has reached operating temperature and is ready for use.

During the warmup period, while the voltage at output terminal 94 is high, both transistors 53 and 84 are switched on. The effect of this is to disable current monitor 26 by shorting its output to ground through transistor 53 and to disable timing oscillator 52 by shorting its input terminal 97 to ground through transistor 84. With the regulator disabled, maximum power is delivered to lamp 1 until the warmup time has elapsed, at which point output terminal 94 of the one-shot multivibrator is switched to ground where it remains until power is removed from the instrument.

When the output of the multivibrator falls to ground at the end of the warming period, transistor 53 is switched off, removing the short from the output of current monitor 26 and effectively reinserting it into the circuit. Simultaneously, transistor 84 is switched off, removing the short from across capacitor 59. However, timing oscillator 52 remains disabled so long as mode switch 90 is actuated in the standby position as shown in FIG. 1, with terminal 91 thereof shorted to ground. This occurs while probe 2 containing lamp 1 is held longitudinally within cradle 151 of the instrument to depress spring loaded switch 90.

During standby operation, a second level of power is delivered to lamp 1, with current therethrough being regulated by current monitor 26 as described above. During this mode of operation, timing oscillator 52 remains disabled by virtue of the connection of resistor 62 across capacitor 59 to ground through switch 90. Resistor 62 is selected to have a value which, when compared to the sum of resistances of resistors 61 and 60, is insufficient to permit capacitor 59 to charge to a voltage large enough to actuate the astable multivabrator within oscillator 52.

Once probe 2 is removed from its holder as shown in FIG. 2, spring loaded switch 90 opens terminal 91 and shorts terminal 63 to ground. Oscillator 52 is no longer disabled and a third level of power is delivered to tube 1. Capacitor 59 is now permitted to charge until it reaches $\frac{2}{3}$ the output voltage of voltage regulator 13 when it thereby actuates the astable multivibrator within timing oscillator 52. Simultaneously, resistor 29 of current monitor 26 is shorted to ground to permit a higher level of current to flow within lamp 1 and thereby produce a greater operating intensity of photocuring light. The components of timing oscillator 52 are selected so that it runs freely and produces current pulses at terminal 104 every 10 seconds. These pulses drive beeper 58 to produce an audible signal which may be used by the dentist to measure curing time of the dental restorative material exposed to the photocuring light from lamp 1.

When probe 2 is replaced within its holder 151, switch 90 is again actuated so that terminal 91 is shorted to ground and the short is removed from across resistor 29. Simultaneously, timing oscillator 52 is inhibited as before and the unit is returned to its standby power operation with power removed from beeper 58.

When the power switch 11 is turned off, capacitor 54 is shorted to ground through terminal 12 of switch 11 so that the unit is ready for triggering the monostable delay oscillator 51 when the power is next switched on.

Capacitors 64, 65 and 66 operate to by-pass any extraneous AC signals that may appear at the output of voltage regulator 13.

As an added safety feature, lamp 1 is coupled to the unit through a plug connector 67 which not only connects it to the secondary of transformer 25 and to the input of current monitor 26, but which also provides a link to complete the circuit from the primary of transformer 25 to ground. In this fashion no high voltage output power can appear at the secondary of transformer 25 unless the lamp is plugged in.

To insure reliable starting under all conditions, a starting electrode 68 may be attached to the lamp 1 and connected to the grounded lamp lead as shown. This may be a very thin wire wrapped around the tube in a manner understood by those versed in the art.

It is to be understood that the above described arrangements are illustrative of the application of the principles of the invention. Numerous other arrangements may be devised by those skilled in the art without departing from the spirit and scope of the invention.

What we claim is:

1. An instrument for delivering radiant energy to a target comprising a fluorescent lamp; power means coupled to said lamp for generating energizing current pulses, including a converter to convert AC line power to rectified DC; a pulse generating oscillator coupled to said converters, including a long time constant resistor-capacitor network for controlling the pulse width of said oscillator; means for detecting the average value of said energizing current connected to said lamp; and an amplifier connected between the output of said detecting means and said network responding directly to the magnitude of said energizing current as detected by said detecting means to adjust directly and continuously the charging rate of said network.

2. An instrument in accordance with claim 1 further comprising delay means coupled to said detecting means for disabling said detecting means to permit maximum energizing current flow within said lamp during a predetermined warmup period.

3. An instrument in accordance with claim 2 further comprising means coupled to said delay means for visually indicating the completion of said warmup period.

4. An instrument in accordance with claim 2 wherein said means for disabling said detecting means comprises a one-shot multivibrator energized by said power means and switching means connected between said multivibrator and said detecting means for disabling said detecting means until said multivibrator switches its output state.

5. An instrument in accordance with claim 2 further comprising switching means connected to said detecting means for selectively energizing said lamp with a standby level and a higher operating level of said energizing current.

6. An instrument in accordance with claim 5 wherein said lamp is contained within a probe, said switching means comprises a two position spring actuated switch situated in a receiving cradle of said instrument and wherein said switch is actuated in a first position to energize said lamp with said standby level of energizing current when said probe is held within said cradle and said switch is actuated in a second position to energize said lamp with said higher operating level of energizing current when said probe is removed from said cradle.

7. An instrument in accordance with claim 6 further comprising a timing circuit energized from said power means for cyclically producing output pulses, an audible tone producing means connected to and energized from said timing circuit and means for coupling said switching means to said timing circuit to disable said timing circuit when said probe is placed within said cradle to actuate said switching means in said first position.

8. An instrument in accordance with claim 7 further comprising a shield covering said lamp to filter out erythemal radiation, a one-shot multivibrator, a voltage regulator connected between said converter and said vibrator and timing circuit, a switching transistor controlled by the output of said multivibrator connected across the output of said detecting means for disabling said detecting means until said multivibrator switches its output state, and wherein said lamp is coated internally with a phosphor material emitting radiant energy having a spectral distribution peaked above erythemal wavelengths, and wherein a light emitting indicator is connected between said regulator and the output of said multivibrator energized when said multivibrator switches its output state.

* * * * *